United States Patent
Ikejima et al.

(10) Patent No.: US 12,000,819 B2
(45) Date of Patent: Jun. 4, 2024

(54) GAS CONCENTRATION PREDICTION METHOD

(71) Applicants: DAIKIN INDUSTRIES, LTD., Osaka (JP); THE UNIVERSITY OF TOKYO, Tokyo (JP)

(72) Inventors: Ikumi Ikejima, Osaka (JP); Hiroshi Matsumoto, Osaka (JP); Kohei Sawada, Tokyo (JP)

(73) Assignees: DAIKIN INDUSTRIES, LTD., Osaka (JP); THE UNIVERSITY OF TOKYO, Tokyo (JP)

( * ) Notice: Subject to any disclaimer, the term of this patent is extended or adjusted under 35 U.S.C. 154(b) by 648 days.

(21) Appl. No.: 17/261,212

(22) PCT Filed: Jul. 25, 2019

(86) PCT No.: PCT/JP2019/029140
§ 371 (c)(1),
(2) Date: Jan. 19, 2021

(87) PCT Pub. No.: WO2020/022413
PCT Pub. Date: Jan. 30, 2020

(65) Prior Publication Data
US 2021/0285926 A1    Sep. 16, 2021

(30) Foreign Application Priority Data
Jul. 25, 2018  (JP) .................. 2018-139560

(51) Int. Cl.
*G01N 33/18* (2006.01)
*G01N 30/02* (2006.01)

(52) U.S. Cl.
CPC ......... *G01N 33/1826* (2013.01); *G01N 30/02* (2013.01); *G01N 2030/025* (2013.01)

(58) Field of Classification Search
CPC ............... G01N 33/1826; G01N 30/02; G01N 2030/025; G01N 33/0049; G01N 2033/0019; G01N 33/0006; G01N 33/0098; G01N 33/02; G01N 33/18; G01N 33/487
See application file for complete search history.

(56) References Cited

U.S. PATENT DOCUMENTS

| | | | |
|---|---|---|---|
| 2015/0082864 A1* | 3/2015 | Chen | G01N 1/2202 73/19.12 |
| 2020/0333317 A1* | 10/2020 | Virtanen | G01N 33/0059 |
| 2021/0148887 A1 | 5/2021 | Ikejima et al. | |
| 2021/0215653 A1* | 7/2021 | Aponte Torrealba | G01N 33/0027 |

FOREIGN PATENT DOCUMENTS

| | | | | |
|---|---|---|---|---|
| CN | 101580869 A | 11/2009 | | |
| CN | 106124647 A | * 11/2016 | ............ | G01N 30/02 |
| CN | 107121553 A | 9/2017 | | |
| JP | 2003-510093 A | 3/2003 | | |
| JP | 2005-523022 A | 8/2005 | | |
| JP | 2013-039099 A | 2/2013 | | |
| WO | 01/23886 A1 | 4/2001 | | |
| WO | 03/089635 A1 | 10/2003 | | |

OTHER PUBLICATIONS

U.S. Appl. No. 17/255,798, Ikumi Ikejima, et al., filed Dec. 23, 2020.
Bothun et al., "Molecular and Phase Toxicity of Compressed and Supercritical Fluids in Biphasic Continuous Cultures of *Clostridium thermocellum*", Biotechnology and Bioengineering, vol. 89, No. 1, Nov. 11, 2004, pp. 32-41 (10 pages total).
Extended European Search Report dated Feb. 15, 2022 from the European Patent Office in EP Application No. 19826191.9.
Extended European Search Report dated Mar. 23, 2022 from the European Patent Office in EP Application No. 19841930.1.
Shiraishi et al., "Study on the Screening Test of Genotoxicity to Volatile and Insoluble Compounds such as Halon Replacements Using Mammalian Cell Culture", Journal of Environmental Chemistry, 1996, vol. 6, No. 2, pp. 217-224.
Akiko Furuyama, "Gas-liquid interface cell exposure device that directly exposes air pollutants to cells", National Institute for Environmental Studies, Oct. 31, 2013, Retrieved from :URL: <https://www.nies.go.jp/kanko/news/32/32-4/32-4-03.html>(10 pages total).
Wolfram E. Samlowski et al., "Nitric Oxide Exposure Inhibits Induction of Lymphokine-Activated Killer Cells by Inducing Precursor Apoptosis", Nitric Oxide: Biology and Chemistry, 1998, pp. 45-56, vol. 2, No. 1, Article No. NO980169.
Kikuo Komori et al., "Simplified Toxicity Evaluation for Gaseous Sample Based on In vitro Bioassay", Monthly Journal of the Institute of Industrial Science, pp. 89-92, 2007, vol. 59, No. 2.
International Search Report of PCT/JP2019/025400 dated Sep. 10, 2019 [PCT/ISA/210].
International Search Report of PCT/JP2019/029140 dated Oct. 15, 2019 [PCT/ISA/210].

* cited by examiner

*Primary Examiner* — Francis C Gray
(74) *Attorney, Agent, or Firm* — Sughrue Mion, PLLC

(57) ABSTRACT

A gas concentration prediction method which includes: step 1 of exposing a gas to a specimen A which contains a liquid containing a compound, and to a specimen B which includes a liquid containing the compound in a concentration lower than the concentration of the compound in the specimen A, under the same conditions X, and step 2 of measuring a gas concentration a in the specimen A obtained in step 1, and a gas concentration b in the specimen B obtained in step 1, to obtain a coefficient α by calculating the relationship between a and b based on the calculation equation $\alpha = a/b$.

3 Claims, No Drawings

GAS CONCENTRATION PREDICTION METHOD

CROSS REFERENCE TO RELATED APPLICATIONS

This application is a National Stage of International Application No. PCT/JP2019/029140, filed Jul. 25, 2019, claiming priority to Japanese Patent Application No. 2018-139560, filed Jul. 25, 2018.

TECHNICAL FIELD

The present disclosure relates to a gas concentration prediction method.

BACKGROUND ART

From the viewpoint of environmental sanitation and food hygiene, the establishment of technology for measuring the concentrations in liquids of various substances that may have toxicity is required.

Of these substances, measuring the concentration of a gas is particularly difficult because the concentration of a gas dissolved in a liquid is very low. In addition, if the liquid contains a compound other than the gas, removal of the compound or concentration of the liquid is required.

SUMMARY OF INVENTION

Technical Problem

In light of the above circumstances, an object of the present disclosure is to provide a method for predicting the concentration of a gas dissolved in a compound-containing liquid, without removing the compound in the liquid or concentrating the liquid.

Solution to Problem

As a result of extensive research to achieve the above object, the inventors found that the step of removing a compound or concentrating a liquid can be omitted by calculating a predetermined coefficient. Based on this finding, the inventors conducted further research, and the present invention was accomplished.

Specifically, the present disclosure provides the following gas concentration prediction methods.

Item 1. A gas concentration prediction method comprising:
  step 1 of exposing a gas to a specimen A comprising a liquid containing a compound, and to a specimen B comprising a liquid containing the compound in a concentration lower than the concentration of the compound in the specimen A, under the same conditions X, and
  step 2 of measuring a gas concentration a in the specimen A obtained in step 1, and a gas concentration b in the specimen B obtained in step 1 to obtain a coefficient $\alpha$ by calculating the relationship between a and b based on the calculation equation $\alpha=a/b$.

Item 2. The method according to Item 1, further comprising:
  step 3 of exposing, under conditions Y, the gas to a specimen B' containing the compound in the same concentration as the specimen B,
  step 4 of measuring a gas concentration b' in the specimen B' obtained in step 3, and
  step 5 of predicting, based on the gas concentration b' and the coefficient $\alpha$, a gas concentration a' in a specimen A' obtained when the gas is exposed to the specimen A' under the conditions Y.

Item 3. The method according to Item 1 or 2, wherein the specimen A is one or more members selected from the group consisting of cell culture medium, river water, industrial waste water, foods, specimens derived from a living subject, and plant extracts.

Item 4. The method according to any one of Items 1 to 3, wherein the gas is at least one member selected from the group consisting of inorganic gases, fuel gases, exhaust gases, and other organic compounds whose main skeleton has a carbon number of 10 or less.

Advantageous Effects of Invention

According to the gas concentration prediction method of the present disclosure, the concentration of a gas dissolved in a liquid containing a compound can be predicted without removing the compound in the liquid or concentrating the liquid.

DESCRIPTION OF EMBODIMENTS

The gas concentration prediction method of the present disclosure comprises step 1 of exposing a gas to a specimen A comprising a liquid containing a compound, and to a specimen B comprising a liquid containing the compound in a concentration lower than the concentration of the compound in the specimen A, under the same conditions X, and
  step 2 of measuring a gas concentration a in the specimen A obtained in step 1, and a gas concentration b in the specimen B obtained in step 1 to obtain a coefficient $\alpha$ by calculating the relationship between a and b based on the calculation equation $\alpha=a/b$.

Step 1

In step 1, the gas is exposed, under the same conditions X, to a specimen A comprising a liquid that contains a compound; and to a specimen B comprising a liquid that contains the compound in a concentration lower than the concentration of the compound in the specimen A.

In the liquid containing a compound, the compound may be completely dissolved, may not be completely dissolved, or may be present as a solid in the liquid without being dissolved at all.

Examples of specimen A include one or more members selected from the group consisting of cell culture liquids (medium), river water, industrial waste water, foods, specimens derived from a living subject, and plant extracts; the specimen A is not limited to these examples. The same applies to the specimen B. In other words, it is preferable that both the specimens A and B are each one or more members selected from the group consisting of cell culture liquids (medium), river water, industrial waste water, foods, specimens derived from a living subject, and plant extracts. The specimens derived from a living subject may be derived from a human or an animal. There is no limitation thereto; examples include blood, plasma, serum, urine, saliva, spinal fluid, bile, sweat, and tears.

The specimen A comprises the liquid containing a compound, as mentioned above. The specimen A is preferably the liquid containing a compound itself; however, the specimen A may be formed by adding other component(s) to the liquid containing a compound.

In the specimens A and B, the liquid containing a compound is preferably a substance that is liquid at room temperature. There is no limitation thereto. Examples include one or more members selected from the group consisting of inorganic solvents, such as water (pure water) and liquid ammonia; and organic solvents, such as alcohols, ethers, and ketones.

The specimen B comprises a liquid in which the concentration of the compound is lower than the concentration of the compound contained in the specimen A. The specimen B may not contain the compound at all. When the specimen A comprises component(s) other than the above compound, it is preferable that the specimen B also contains the same component(s) in the same concentration(s).

As conditions for gas exposure, the same conditions X are used for the specimen A and the specimen B.

Conditions X may be suitably determined according to the purpose of the measurement and the like, without limitation. For example, the temperature condition is preferably between −20 and 200° C. The exposure may be performed in a closed system or an open system; if the exposure is performed in a closed system, it is preferable to set the pressure to 101.3 kPa or more.

The gas is not limited. Examples include one or more gases selected from the group consisting of inorganic gases, fuel gases, exhaust gases, and other organic compounds (gaseous organic compounds) whose main skeleton has a carbon number of 10 or less.

Examples of inorganic gases include helium, hydrogen, oxygen, nitrogen, carbon monoxide, nitrogen, fluorine, chlorine, bromine, phosgene, phosphine, hydrogen sulfide, hydrogen chloride, hydrogen fluoride, and ammonia.

Examples of fuel gases include methane, propane, butane, and acetylene.

Examples of exhaust gases include hydrocarbons, nitrogen oxides, and sulfur oxides.

Examples of organic compounds (gaseous organic compounds) whose main skeleton has a carbon number of 10 or less include acetone, benzene, toluene, xylene, formaldehyde, and dichloromethane.

There is no limitation to the method of exposing the gas to the specimens A and B, and a wide range of known methods can be used. Examples include a method of bubbling a gas into a specimen, a method of flowing a gas onto the liquid surface of a specimen, and a method of placing a specimen under a gas atmosphere.

The conditions X are conditions that are set for exposing the gas is to the specimens A and B. Examples of conditions X include the exposure time; and the gas concentration, gas pressure, temperatures of specimens A and B, etc., in the exposure.

Step 2

In Step 2, the gas concentration a in the specimen A obtained in step 1 and the gas concentration b in the specimen B obtained in step 1 are measured, thus obtaining the coefficient $\alpha$ by calculating the relationship between a and b based on the calculation equation $\alpha=a/b$.

There is no limitation to the method for measuring the gas concentration in the specimens A and B. A wide variety of known methods for measuring the concentration of a gas dissolved in a liquid can be used. Specifically, a method selected from the group consisting of gas chromatography, mass spectrometry, visible UV spectroscopy, absorption spectroscopy, infrared spectroscopy, Raman spectroscopy, and nuclear magnetic resonance can be used.

The correction coefficient $\alpha$ is not limited, as long as it is a coefficient that defines the relative value of the gas concentrations a and b. For example, it is preferable that the coefficient is calculated by the calculation equation $\alpha=a/b$.

After obtaining the correction coefficient as described above, it is preferable to measure the gas concentration in the specimen comprising a liquid not containing the above compound, and to predict the gas concentration in the liquid containing the compound based on the measured value and the correction coefficient $\alpha$.

More specifically, it is preferable that the gas concentration prediction method of the present disclosure further includes, after steps 1 and 2, step 3 of exposing, at conditions Y, the gas to a specimen B' that contains the compound in the same concentration as the specimen B, step 4 of measuring the gas concentration b' in the specimen B' obtained in step 3, and step 5 of predicting the gas concentration a' in the specimen A' obtained when the gas is exposed to the specimen A' under the conditions Y, based on the gas concentration b' and the coefficient $\alpha$.

Step 3

In step 3, the gas is exposed, at conditions Y, to the specimen B' containing the compound in the same concentration as the specimen B.

The specimen A' comprises the liquid containing a compound. In this specification, the liquid containing a compound in step 3 may be substantially formed of the same composition as the liquid containing a compound in step 1. The substantially same composition in this specification is defined as the concentration of a compound contained in the specimen A' being within the ±1 mass % range of error of the concentration of the compound contained in the specimen A.

The specimen B' comprises a liquid that contains the compound in the same concentration as the specimen B. In this specification, the specimen B' containing the compound in the same concentration as the specimen B is defined as the concentration of the compound in the specimen B' being within the ±1 mass % range of error of the concentration of the compound contained in the specimen B.

In step 3, the gas to be exposed to the specimens A' and B' is the same as the gas used in step 1.

As a method for exposing the gas, it is preferable to use the same method as that employed in step 1.

In order to accurately predict the gas concentration, the conditions Y are preferably the same as the conditions X in step 1; however, the conditions Y may be different from the conditions X.

Step 4

In step 4, the gas concentration b' in the specimen B' is measured.

Although there is no limitation to the method of measuring the gas concentration, widely known methods can be used. From the viewpoint of accurately predicting the gas concentration, it is preferable to use the same method as the gas concentration measuring method used in step 2.

Step 5

In step 5, based on the gas concentration b' and the coefficient $\alpha$, the gas concentration a' in the specimen A' obtained when the gas is exposed to the specimen A' under the conditions Y is predicted.

The gas concentration a' can be calculated by using the gas concentration b' and the correction coefficient $\alpha$. For example, when the correction coefficient $\alpha$ is obtained by the calculation equation $\alpha=a/b$ in step 2, the gas concentration a' can be obtained by multiplying the gas concentration b' by the correction coefficient $\alpha$.

The gas concentration prediction method of the present disclosure as described above can accurately predict the concentration of a gas dissolved in a liquid containing a compound while omitting the step of directly measuring the concentration of the gas dissolved in the liquid containing a compound by utilizing the correction coefficient α above.

Thus, embodiments of the present invention are explained; however, the present invention is not limited to these examples. It is, of course, possible to practice the invention in various forms, to the extent that these forms do not deviate from the gist of the present invention.

EXAMPLES

Based on the following example, embodiments of the present invention are described in more detail below; however, the present invention is not limited thereto.

Example

The gas shown in Table 1 was bubbled at 20 mL/min for 1 minute in 5 mL of a cell culture medium (liquid containing 6.4 g/L of sodium chloride, 4.7 g/L of D-glucose, 3.7 g/L of sodium bicarbonate, L-lysine hydrochloride, 0.84 g/L of L-arginine hydrochloride, 0.58 g/L of L-glutamine, and 0.3 g/L of calcium chloride) or in 5 mL of purified water, at a liquid temperature of 23° C.; and dissolved. Subsequently, the concentration of a gas dissolved in the cell culture liquid or pure water was measured by gas chromatography (Shimadzu Corporation). Each measurement was repeated three times, and the average gas concentration was calculated. The correction coefficient α was then obtained by dividing the average gas concentration in the cell culture liquid by the average gas concentration in the pure water.

TABLE 1

| Gas | Gas concentration/ppm | | Correction coefficient α |
|---|---|---|---|
| | Cell culture liquid | Pure water | |
| $CHF_2Cl$ | 1785 | 2399 | 1.34 |
| $CH_2F_2$ | 2972 | 4140 | 1.39 |
| $CH_2F—CF_3$ | 529 | 656 | 1.24 |
| $CF_3—CF=CH_2$ | 262 | 331 | 1.26 |

At a later date, the same measurements as above were performed, and the correction coefficient was calculated in the same manner. The results are shown in Table 2.

TABLE 2

| Gas | Gas concentration/ppm | | Correction coefficient α |
|---|---|---|---|
| | Cell culture liquid | Pure water | |
| $CHF_2Cl$ | 1820 | 2421 | 1.33 |
| $CH_2F_2$ | 2701 | 3673 | 1.36 |
| $CH_2F—CF_3$ | 599 | 755 | 1.26 |
| $CF_3—CF=CH_2$ | 288 | 360 | 1.25 |

Tables 1 and 2 proved that the measurement values of the correction coefficient α mean extremely high reproducibility. Accordingly, it is found that the prediction of gas concentration using the correction coefficient α enables the prediction of the concentration of the gas dissolved in the cell culture liquid (liquid containing a compound) with high accuracy, without measuring the concentration of the gas dissolved in the liquid containing a compound. Thus, predicting the gas concentration using the correction coefficient α can reduce the opportunities of actually measuring the concentration of a gas dissolved in a liquid containing a compound, such as a cell culture liquid. As a result, the load on the measuring equipment can be reduced, which minimizes measuring equipment malfunction.

The invention claimed is:

1. A gas concentration prediction method comprising:
    step 1 of exposing a gas to a specimen A comprising a liquid containing a compound, and to a specimen B comprising a liquid containing the same compound in a concentration lower than the concentration of the compound in the specimen A, under the same conditions X,
    wherein if the specimen A contains other components in addition to the gas and the compound, the specimen B contains the same components at the same concentrations as the specimen A;
    step 2 of measuring a gas concentration a in the specimen A obtained in step 1, and a gas concentration b in the specimen B obtained in step 1, to obtain a coefficient α by calculating the relationship between a and b based on the calculation equation α=a/b;
    step 3 of exposing, under conditions Y, the gas to a specimen B' containing the same compound in the same concentration as the specimen B;
    step 4 of measuring a gas concentration b' in the specimen B' obtained in step 3; and
    step 5 of predicting, based on the gas concentration b' and the coefficient α, a gas concentration a' in a specimen A' obtained when the gas is exposed to the specimen A' under the conditions Y according to the formula a'=ab',
    wherein specimen A' contains the same compound in a concentration within the ±1 mass % range of error of the concentration as the specimen A, and
    wherein if the specimen B' contains other components in addition to the gas and the compound, the specimen A' contains the same components at the same concentrations as the specimen B', and
    wherein the concentrations of the compound in specimen A, B, A' and B' are known.

2. The method according to claim 1, wherein the specimen A is at least one member selected from the group consisting of cell culture medium, river water, industrial waste water, foods, specimens derived from a living subject, and plant extracts.

3. The method according to claim 1, wherein the gas is one or more members selected from the group consisting of inorganic gases, fuel gases, exhaust gases, and other organic compounds whose main skeleton has a carbon number of 10 or less.

* * * * *